(12) United States Patent
Molloy

(10) Patent No.: US 6,194,194 B1
(45) Date of Patent: Feb. 27, 2001

(54) METHOD FOR CONTROLLING DREISSENA SPECIES

(76) Inventor: Daniel Molloy, R.D. 2, Conley Rd., Cambridge, NY (US) 12816

( * ) Notice: Subject to any disclaimer, the term of this patent is extended or adjusted under 35 U.S.C. 154(b) by 0 days.

(21) Appl. No.: 08/992,040

(22) Filed: Dec. 17, 1997

Related U.S. Application Data

(60) Provisional application No. 60/033,818, filed on Dec. 23, 1996.

(51) Int. Cl.[7] .............................. C12N 1/20; C07G 17/00
(52) U.S. Cl. ....................... 435/253.3; 435/267; 435/876
(58) Field of Search .............................. 435/253.3, 267, 435/876

(56) References Cited

PUBLICATIONS

"Helminth and protist parasites of zebra mussels, Dreissen polymorpha (Pallas, 1771), in the Great Lakes region region of southwestern Ontario, with comments on associated bacteria," by Sheila Toews, Beverly–Burton, and Tara Lawrimore; Can. J. Zool., vol. 71 (1993), pp. 1762–1766.

*Primary Examiner*—Laurie Scheiner
(74) *Attorney, Agent, or Firm*—Heslin & Rothenberg, P.C.

(57) ABSTRACT

A method for controlling Dreissena species, including, but not limited to, zebra (*D. polymorpha*) and quagga (*D. bugensis*) mussels, by use of a toxin-producing microorganism having the identifying characteristics of Pseudomonas ATCC 55799 is disclosed.

17 Claims, No Drawings

METHOD FOR CONTROLLING DREISSENA SPECIES

This application claims benefit under 35 U.S.C. Section 119(e) of Provisional Application 60/033,818, filed Dec. 23, 1996, now expired.

FIELD OF THE INVENTION

This invention relates to a method for controlling Dreissena species, including, but not limited to, zebra (*D. polymorpha*) and quagga (*D. bugensis*) mussels, by use of a toxin-producing microorganism.

BACKGROUND OF THE INVENTION

Zebra mussels are small molluses of the Dreissena genus native to European water bodies and have recently been detected in large numbers in North America.

The spread of Dreissena species is of great concern to municipal, utility, and environmental interests because of the propensity of these species to form thick colonies. The formation of these colonies can have many effects, such as, for example, occluding structures such as water intake pipes, thus reducing the volume of water delivered, and degrading water quality and purity. Widespread unchecked colonization of Dreissena therefore threatens the operation of such industries as power plants, which rely on raw water for operation. In addition, Dreissena species kill many native bivalves such as unionid mussels, and the like, as well as consume ecologically important microscopic plankton.

Mechanical removal of the colonies is difficult and costly. Filtration of large volumes of intake water is impractical considering the small size (40 to 290 microns) of the colonizing larvae. Thermal or chemical treatment (e.g. hot water or chlorine) of intake water can be effective, but may have undesirable environmental consequences in some large-scale operations. Regulatory agencies continue to warn industries that continued long-term use of chemical and thermal control methods will be limited. A practical and economical method that reduces Dreissena colonization without adverse environmental impacts is therefore highly desirable.

The use of microorganisms such as bacteria or their chemical products to control pest populations is well known in the art. *Bacillus thuringiensis* varieties, for example, have been used for many years as a commercial insecticide for lepidopteran pests. More recently, additional strains of *B. thuringiensis* have been discovered which have specificity for an expanded range of pest populations, including, for example, mosquitoes, black flies, beetles, and the like.

Another bacterium, *Serratia liquefaciens*, has been shown to be lethal to zebra mussels (Toews et al., *Can J Zool.*, Vol. 71, 1763 (1993)). To date, however, there has been no recognition of a strain of Pseudomonas that has a demonstrated ability to specifically control Dreissena species.

SUMMARY OF THE INVENTION

In one embodiment, the present invention relates to a *Pseudomonas fluorescens* biotype A (American Type Culture Collection Project Report SC3738 Bacterial Characterization; biotype A as follows Stanier, J., *Gen. Microbiol.*, Vol. 43, 159 (1966)) isolate CL0145A, hereinafter, "ATCC 55799," that is toxic to Dreissena and can therefore be used to control them.

In another embodiment of the present invention, variants of the *Pseudomonas fluorescens* isolate that have substantially the same molluscicidal properties as the isolate can also be used to control Dreissena species. Such variants can include, but are not limited to, mutants, whether spontaneously occuring or that are induced chemically or by other means well known in the art. Spontaneous mutant strains of an organism can arise naturally, as the cells in the organism divide and proliferate. Each time a cell divides, there is a small probability of an inheritable change in the DNA (ie., an alteration in a particular amino acid sequence of a protein within the DNA chain) of the organisim and such changes, unless lethal to the organism, will give rise to a mutant strain of the organism. In addition, it is often desired to deliberately introduce or induce a particular mutation into an organism, in an attempt to produce an improved strain having the characteristic associated with the mutation. Induced mutations may be achieved by such means known in the art as UV radiation, ionizing radiation, or chemicals such as nitric acid.

In addition, organisms other than the exemplified *Pseudomonas fluorescens* isolate into which the Dreissena toxin-producing genes of the isolate have been transferred, such as, for example, by transduction, transformation or other genetic engineering means, wherein the genetically engineered organism achieves the same molluscicidal properties as the isolate, can also be used to control Dreissena.

In accordance with the principles of the present invention, organisms other than the exemplified *Pseudomonas fluorescens* isolate, which have he toxin-producing characteristics of Pseudomonas ATCC 55799, can also be used to control Dreissena species.

The present invention also includes a method for controlling Dreissena species by using one or more of the ATCC 55799 strain itself, variants or mutants of the ATCC 55799 strain, fragments and toxins of the ATCC 55799 strain that retain pathogenicity to Dreissena, organisms into which the ATCC 55799 strain toxin-producing genes have been genetically transferred, and organisms other than the ATCC 55799 strain which have the toxin-producing characteristics of the ATCC 55799 strain.

DETAILED DESCRIPTION OF THE INVENTION

The novel *Pseudomonas fluorescens* isolate, ATCC 55799, of the present invention has the following characteristics in its biologically pure form:

Cellular Morphology

Gram-negative, short to long rods that appear singly and many in pairs. Motile by a polar tuft flagella (multitrichous polar flagella).

Colony Morphology

Isolate has two colony types, (a) 98% circular, convex, entire edge, smooth to rough appearance, a little bigger than colony type "b" and translucent in opacity; and (b) 2% compact, circular, entire edge, smooth, convex and opaque in opacity. Strain exhibits very strong beta-hemolysis on blood agar.

Some of the growth characteristics of *Pseudomonas fluorescens* on different media and under various conditions are illustrated in Tables 1–3, wherein (+) indicates positive growth or the presence of the indicated characteristic; and (−) indicates the absence of growth or the indicated characteristic.

TABLE 1

ATCC 55799 Characterization Data

| | | | |
|---|---|---|---|
| Gram positive | − | starch hydrolysis | − |
| Gram negative | + | gelatinase (plate) | + |
| Gram variable | − | Tween 20 ® hydrolysis | + |
| motile | + | Tween 80 ® hydrolysis | + |
| flagella peritrichous | − | indole | − |
| flagella lophotrichous | + | simmons citrate growth | + |
| flagella monotrichous | − | urease | − |
| flagella lateral | − | nitrate to nitrite[1] | − |
| 4° C. growth | − | nitrite reduction[1] | − |
| 25° C. growth | + | nitrite to nitrogen gas[1] | − |
| 30° C. growth | + | hydrogen sulfide (TSI)[2] | − |
| 37° C. growth | + | lysine decarboxylase | − |
| 41° C. growth | − | arginine (Mollers) | + |
| fluorescein produced | + | ornithine decarboxylase | − |
| pyocyanine produced | − | phenylalanine deamination | − |
| diffusible orange | − | lecithinase | + |
| diffusible yellow | − | phosphatase | + |
| diffusible purple | − | catalase | + |
| non-diffusible green | − | oxidase | + |
| other non-diffusible pigments | − | gluconate oxidation | − |
| diffusible brown (melanin) | − | growth on malonate as SCS | + |
| pH 6.0 growth | + | tyrosine degradation | + |
| 3% NaCl growth | + | dl-hydroxybutyrate growth | + |
| 6.5% NaCl growth | − | PHB accumulation | − |
| MacConkey agar growth | + | deoxyribonuclease | − |
| skim milk agar growth | + | growth on 0.05% cetrimide | + |
| aesculin hydrolysis | − | growth on acetate as SCS | + |
| casein hydrolysis | + | testosterone degradation | − |

[1]A major distinguishing characteristic of biotype A is the inability to denitrify.
[2]lead acetate strip
Zn dust was added to nitrate reduction for the final reading.

These results characterize the *Pseudomonas fluorescens* ATCC 55799 isolate in that it is a gram negative short to long rod; is motile by polar tuft of three or more flagella (lophotrichous); it produces a fluorescent, yellow-green pigment (pyoverdin); and it does not produce pyocyanin.

TABLE 2-1

Hugh and Leifson Oxidation/Fermentation Medium

| Acid from: | | Acid from: | |
|---|---|---|---|
| L-arabinose | + | D-mannitol | + |
| cellobiose | K | D-mannose | + |
| ethanol | W | L-rhamnose | K |
| D-fructose | W | D-ribose | + |
| D-glucose AO$_2$ | + | sucrose | + |
| D-glucose AnO$_2$ | − | trehalose | + |
| glycerol | + | D-xylose | + |
| i-inositol | + | Alkaline pH in D-glucose | − |
| lactose | K | 3-ketolactose from lactose | − |
| maltose | K | CONTROL | K |

(K) indicates alkaline, (W) indicates weakly positive

TABLE 2-2

Additional Characterization using Xanthomonas sp.

| | |
|---|---|
| Mucoid growth on glucose agar | − |
| litmus milk acid | − |
| litmus milk peptonized | + |

TABLE 3

Stanier's Basal Medium

| | | | |
|---|---|---|---|
| L-arabinose as SCS | − | 2-ketogluconate as SCS | + |
| celiobiose as SCS | − | DL-lactate as SCS | + |
| D-fructose as SCS | + | L-malate as SCS | + |
| D-glucose as SCS | + | pelargonate as SCS | + |
| lactose as SCS | − | propionate as SCS | + |
| maltose as SCS | − | quinate as SCS | + |
| D-mannitol as SCS | + | succinate as SCS | + |
| L-rhamnose as SCS | − | L-(+)tartrate as SCS | − |
| D-ribose as SCS | + | valerate as SCS | + |
| D-sorbitol as SCS | − | B-alanine as SCS | + |
| sucrose as SCS | + | D-A-alanine as SCS | + |
| trehalose as SCS | + | betaine as SCS | + |
| D-xylose as SCS | − | glycine as SCS | − |
| adonitol as SCS | − | L-histidine as SCS | + |
| erythritol as SCS | − | DL-norleucine as SCS | + |
| glycerol as SCS | + | L-proline as SCS | + |
| ethanol as SCS | − | D-tryptophan as SCS | − |
| geraniol as SCS | − | L-valine as SCS | + |
| i-inositol as SCS | + | DL-arginine as SCS | + |
| sebacic acid as SCS | + | benzylamine as SCS | + |
| acetamide as SCS | − | butylamine as SCS | + |
| adipate as SCS | + | putrescine as SCS | + |
| benzoate as SCS | + | mesaconate as SCS | − |
| butyrate as SCS | + | DL-glycerate as SCS | + |
| citraconate as SCS | − | L-tryptophan as SCS | + |
| D-gluconate as SCS | + | methanol as SCS | − |
| M-hydroxybenzoate as SCS | − | | |

Inoculum: $1.2 \times 10^3$ mg/mL in a tube with carbon source.

The culture disclosed in this application has been deposited with the American Type Culture Collection (ATCC), 12301 Parklawn Drive, Rockville, Md. 20852 U.S.A. as follows:

| Culture | Repository No. | Deposit Date |
|---|---|---|
| Pseudomonas | ATCC 55799 | July 10, 1996 |

The culture has been deposited under conditions that assure that access to the culture will be available during the pendency of this patent application to one determined by the Commissioner of Patents and Trademarks to be entitled thereto under 37 CFR 1.14 and 35 U.S.C. §122. The deposit is available as required by foreign patent laws in countries wherein counterparts of the subject application, or its progeny, are filed. It should, however, be understood that the availability of the deposit does not constitute a license to practice the principles of the present invention in derogation of patent rights granted by governmental action.

Preferred embodiments of the present invention are hereinafter described in more detail by means of the following examples that are provided by way of illustration and not by way of limitation.

Preparation of ATCC 55799 Cell Suspension

A subculture of *Pseudomonas fluorescens* ATCC 55799 is used to inoculate the growth medium, trypticase soy broth (TSB), methods for the preparation of which are known in the art. The cells are then incubated in 6 mL of TSB at 28° C. for 42 hours. The culture is expanded by adding the 6 mL of the 42-hour culture to a 250 mL flask containing 100 mL of TSB. This flask is incubated at 28° C. for 72 hours. None of the above culturing is done with aeration or agitation.

The cells thus cultured are harvested in the following manner. The culture medium containing the cells is centrifuged at 827 xg for 30 min at room temperature (20–24° C.). The supernatant is poured off and the pellet of cells is resuspended in dilution water (i,e., 80 ppm $KH_2PO_4$ and 406 ppm $MgCl_2 \cdot 6H_2O$ in deionized water).

Zebra Mussel Assay

Toxicity of ATCC 55799 cells to Dreissena is assayed in the following manner. Cells which have been resuspended in water as described above are added to water containing Dreissena mussels to achieve a concentration of about 100 ppm (i.e., 100 mg of bacterial dry mass/liter of water). Water within the tank is recirculated up to five days, and mussel mortality is assessed at that time. The surviving mussels are transferred to water not containing ATCC 55799 cells, and mussel mortality monitored for a minimum of seven days thereafter.

Alternatively, resuspended cells are added at regular time intervals to continuously-flowing water containing Dreissena mussels to maintain a concentration of about 100 ppm (i.e., 100 mg of bacterial dry mass/liter of water). In this case, the water is treated for a minimum of one day.

As an indication of the ability of *Pseudomonas fluorescens* to kill zebra mussels, 92% and 100% mortality were obtained, respectively, when they were exposed to a concentration of at least 42 ppm (i.e., 42 mg of bacterial dry mass/liter of water) in laboratory test chambers for one and five days at 22° C. Control mortality for the same period was $\leq 4\%$.

Characterization of the ATCC 55799 Toxin

When a culture of ATCC 55799 was treated with the antibiotic amikacin, only about 3% of the cells remained alive. Despite the sharp decline in viability of the cells, the bacteria were still capable of causing high zebra mussel mortality; ordinarily, 3% of the cells from a normal live culture does not cause any appreciable Dreissena mortality, indicating that the ability of this bacterial strain to kill mussels does not require live cells.

Treatment of ATCC 55799 with lysozymes causes the cell wall of the organism to be digested with a concomitant loss of ability to kill Dreissena. Since the disruptive action of the lysozyme treatment is restricted to the cell wall, bacteria treated with lysozymes remain alive, but are non-lethal to Dreissena. This indicates that the toxin effects are associated with the cell wall of the bacterium. The toxin may also have more than one component.

Histological tissue sections from Dreissena dying from exposure to ATCC 55799 cultures were examined. No bacterial cells were observed associated with any tissues. Main organs, such as the gills, were normal in appearance; the digestive gland, which typically is involved with detoxification, showed severe signs of tissue disruption and destruction. This histological analysis demonstrates that killing of the mussels is toxin-mediated rather than by bacterial infection.

When ATCC 55799 cells are subjected for 30 min to 50° C., the ability to kill Dreissena is lost, indicating that the toxin is heat labile at temperatures $\geq 50°$ C.; a characteristic common to protein toxins.

In the methods of the present invention, a cell suspension comprising cells having the toxin-producing characteristics of ATCC 55799 is prepared in accordance with the previous examples and then introduced into a body of water, known to contain Dreissena species, in an amount effective to control the Dreissena species. Thus, the present invention provides an effective method for controlling Dreissena species in their natural environment.

This invention has been described in terms of specific embodiments, set forth in detail. It should, however, be understood that these embodiments are presented by way of illustration only, and that the invention is not necessarily limited thereto. Modifications and variations within the spirit and scope of the claims that follow will be readily apparent from this disclosure, as those skilled in the art will appreciate.

I claim:

1. A Pseudomonas strain, having the identifying characteristics of Pseudomonas ATCC 55799.

2. A zebra mussel toxin, derived from an organism of claim 1.

3. A zebra mussel toxin, associated with the cell wall of an organism of claim 1.

4. A quagga mussel toxin, derived from an organism of claim 1.

5. A quagga mussel toxin, associated with the cell wall of an organism of claim 1.

6. A method for controlling Dreissena species, said method comprising the steps of:
    (a) preparing a cell suspension comprised of cells having the toxin-producing characteristics of Pseudomonas ATCC 55799; and
    (b) introducing said suspension into a body of water containing Dreissena species, in an amount effective to control said Dreissena species.

7. The method according to claim 6 wherein the cell suspension comprises cells of a strain of Pseudomonas.

8. The method according to claim 7 wherein the cell suspension comprises cells of *Pseudomonas fluorescens*.

9. The method according to claim 7 wherein the cell suspension comprises cells of a mutant strain of *Pseudomonas fluorescens*.

10. The method according to claim 6 wherein said Dreissena species is *D. polymorpha*.

11. The method according to claim 6 wherein the Dreissena species is *D. bugensis*.

12. A method for controlling Dreissena species, said method comprising the steps of:
    a) preparing a solution of a toxin isolated from an organism having the identifying characteristics of Pseudomonas ATCC 55799; and
    b) introducing said solution into a body of water containing Dreissena species, in an amount effective to control said Dreissena species.

13. The method according to claim 12 wherein the organism is a strain of Pseudomonas.

14. The method according to claim 13 wherein the organism is *Pseudomonas fluorescens*.

15. The method according to claim 13 wherein the organism is a mutant strain of *Pseudomonas fluorescens*.

16. The method according to claim 12 wherein the Dreissena species is *D. polymorpha*.

17. The method according to claim 12 wherein the Dreissena species is *D. bugensis*.

* * * * *